US00PP18466P2

(12) United States Plant Patent
Falstad

(10) Patent No.: US PP18,466 P2
(45) Date of Patent: Jan. 29, 2008

(54) ***HOSTA* PLANT NAMED 'EYE DECLARE'**

(50) Latin Name: ***Hosta* hybrid (Tratt.)**
Varietal Denomination: Eye Declare

(75) Inventor: Clarence Falstad, Holland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 17 days.

(21) Appl. No.: 11/504,333

(22) Filed: Aug. 15, 2006

(51) Int. Cl.
*A01H 5/00* (2006.01)

(52) U.S. Cl. ..... Plt./353
(58) Field of Classification Search ..... Plt./353
See application file for complete search history.

*Primary Examiner*—Kent Bell

(57) ABSTRACT

A new and distinct *Hosta* plant named 'Paradise Power' characterized by heart-shaped, large-sized, leaves with green margins, viridescent light yellowish leaf centers, vertical flower scapes well above foliage with numerous light lavender flowers, suitable for landscape, potted culture, or cut flower arrangements.

2 Drawing Sheets

Botanical classification: *Hosta* hybrid (Tratt.).
Variety denomination: 'Eye Declare'.

SUMMARY, BACKGROUND AND ORIGIN OF THE PLANT

The new and distinct *Hosta* plant, hereinafter also referred to as 'Eye Declare' and "the plant" is a new and distinct cultivar of *hosta*. It was found by Clarence Falstad in October of 1999 as an un-induced whole plant sport of the *Hosta* cultivar 'Sea Fire' (not patented) at a tissue culture facility at a nursery in Zeeland, Mich. *Hosta* 'Sea Fire' is a hybrid of Mrs. Mildred Seaver formerly of Needham Height, Mass. The plant has been successfully propagated by division and tissue culture methods at the same perennial plant nursery in Zeeland, Mich. and found to produce identical plants that maintain the unique characteristics of the original plant. The plant is stable and reproduces true to type in successive generations of asexual reproduction.

*Hosta* 'Eye Declare' differs from its parent sport, 'Sea Fire' as well as all other *hostas* known to the applicant, in that the plant is variegated with a viridescent yellow center emerging in the spring with a very light butter yellow and dark green margin. With warmer summer temperatures the center color gradually develops to a light to medium green. *Hosta* 'Sea Fire' also has another sport: 'St. Elmo's Fire' (not patented), which has the same viridescent yellow center with a white margin.

The most similar known *hosta* cultivar is 'Paradise Power' U.S. Plant Pat. No. 12,117. Both cultivars are yellow with a green margin, but 'Eye Declare' is viridescent and 'Paradise Power' is lutescent. 'Paradise Power' is also much larger and has a longer more pointed leaf than 'Eye Declare'. 'Paradise Power' also does not possess the red stippling that 'Eye Declare' has in the leaf petiole and scape and seed pod. Several other cultivars with yellow leaf centers and green margins also exist, but with fewer similarities to the plant.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

GENERAL DESCRIPTION OF THE PLANT

Figure 1:
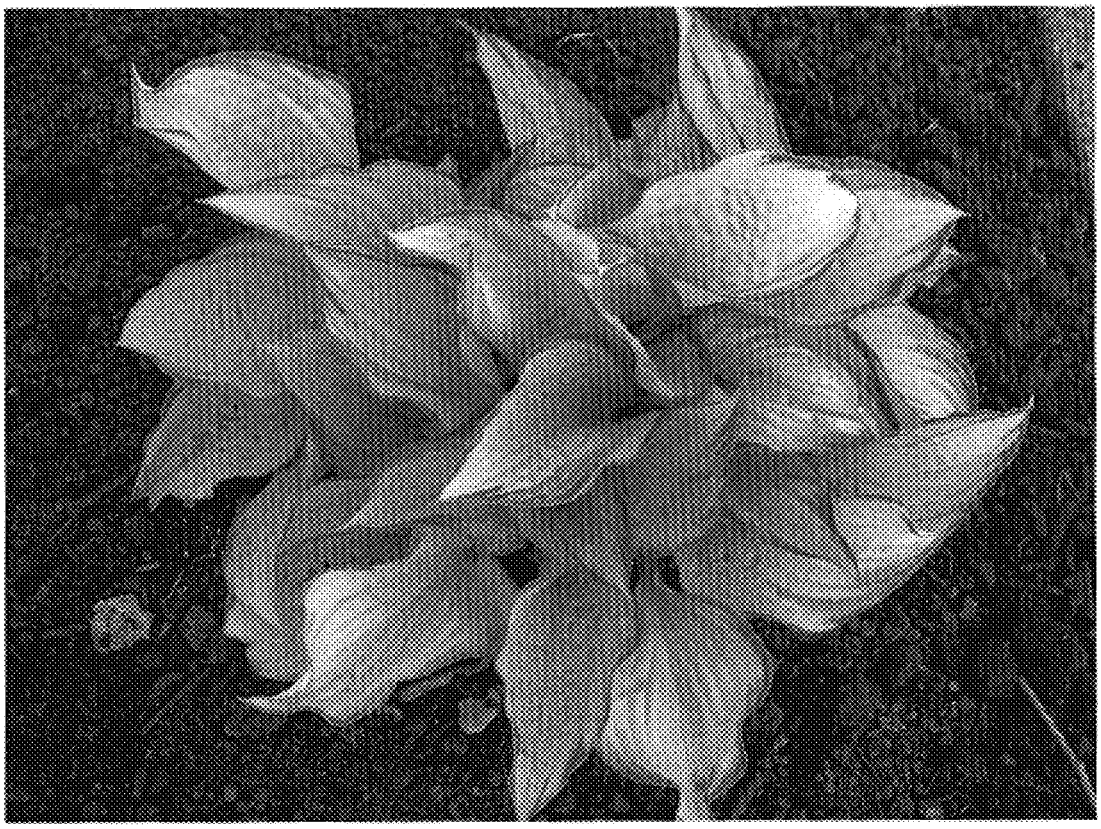
FIG. 1 shows the overall plant early in the season.
Figure 2:
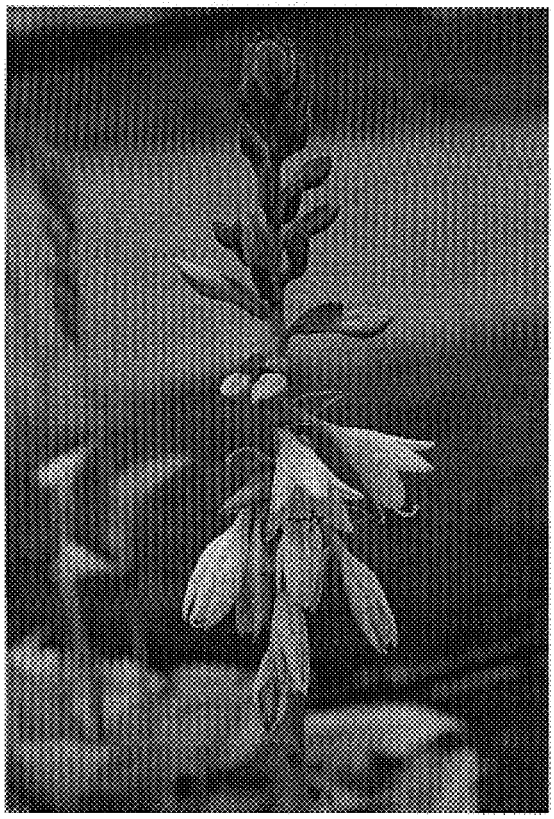
FIG. 2 shows the flower and scape in mid July.
Figure 3:
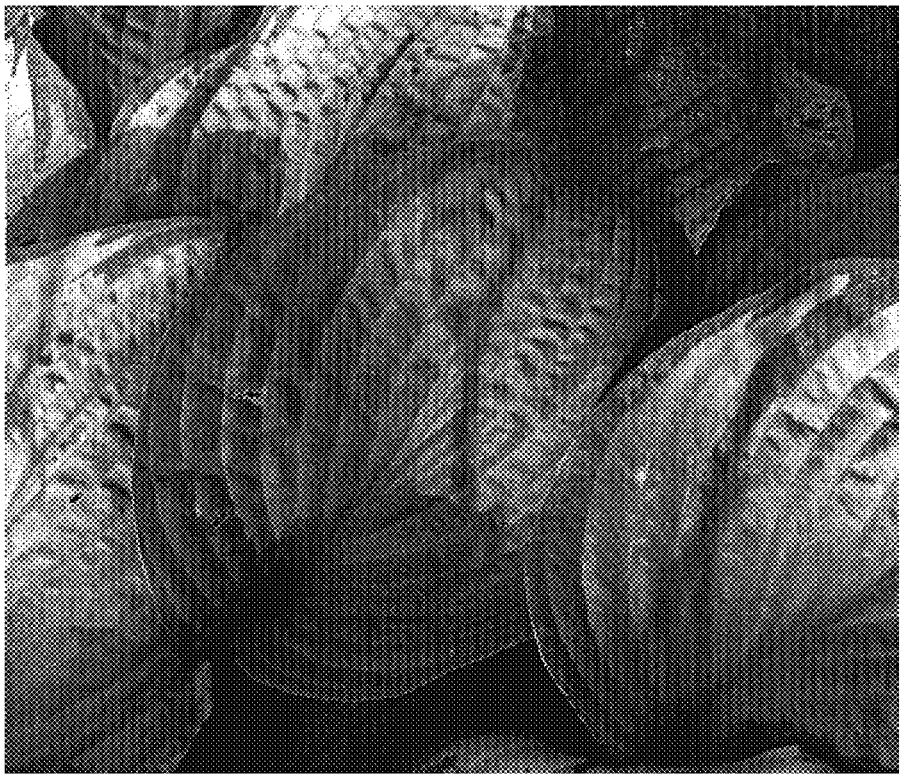
FIG. 3 shows the plant foliage after flowering.

The genus *Hosta* is mainly native to Japan with a few species originating from China and Korea. There are over 3,300 cultivars registered with The American Hosta Society, which is the International Cultivar Registration Authority for the genus *Hosta*. *Hosta* 'Eye Declare' differs from all of these known to the inventor in that it has:

1. Light yellow foliage early in the season margined with a dark green border
2. Pendulous light lavender flower on scapes well above foliage.
3. Red stippling on leaf petioles and flower scape.

DETAILED BOTANICAL DESCRIPTION

The following descriptions and color references are based on the 2001 edition of The Royal Horticultural Society Colour Chart except where common dictionary terms are used. The new plant, *Hosta* 'Eye Declare', has not been observed under all possible environments. The phenotype may vary slightly with different environmental conditions, such as temperature, light, fertility, moisture and maturity levels, but without any change in the genotype. The following observations and size descriptions are of a four-year old plant in a garden in Zeeland, Mich. under 50% shade cloth with supplemental water and fertilizer.

Botanical classification: *Hosta*×hybrid.
Parentage: Naturally occurring sport of *Hosta* 'Sea Fire' (not patented).
Propagation:
*Method.*—By sterile laboratory tissue culture division and garden division.
*Time to initiate roots from both division and tissue culture.*—Two to three weeks.
*Rooting habit.*—Normal, fleshy, lightly branching.

Plant description:

*Plant shape and habit.*—Hardy herbaceous perennial with basal rosette leaves, symmetrical and arching over.

*Crop time.*—Under normal summer growing conditions about 16 weeks to finish in a one-liter container. Plant vigor is good to high.

*Plant size.*—Foliage height at flowering is 30 to 35 cm tall from soil line to the top of the leaves and 45 to 50 cm wide at soil line.

Foliage description:

*Shape and size.*—Elliptic to cordate leaf blades have an acute apex and rounded base. The leaf blades are 18 to 20 cm long and 12 to 14 cm wide. The leaf blade margin is entire and the variegation pattern on the darker edge varies in different regions of the leaf from 2 to 10 mm wide. The leaves have between 10 and 11 pairs of major parallel veins. Top surface is dull without significant glaucous bloom, and bottom surface is shiny. There is a slight dimpling running between the veins.

*Blade color.*—Young emerging leaves: Top surface center and margin respectively: RHS 3B; RHS 141B. Underside center and margin respectively: RHS 3B; RHS 141B or RHS 141C, Some intermediate colors on top and bottom with the major portion between RHS N144A and RHS N144C. Top surface of mature leaves: Top surface center and margin respectively: Between RHS 145C and RHS 157D; RHS 139A. Underside center and margin respectively: between RHS 144A and RHS N144A; between RHS 139A and RHS 141 A. The intermediate color bands on the top and bottom surfaces of mature leaves develop a deeper green less distinguishable from the margin color. In more sun the center color of the mature leaves bleaches to an RHS 157C on the leaf back and between RHS 145 C and RHS 157 D on the top. Veins color is the same as the surrounding leaf tissue on both the top and bottom of the leaf.

*Petioles.*—16 to 18 cm long and 1.0 to 1.4 cm wide. The leaf margin continues down the petiole 1 to 2 mm wide and RHS 141 C on young foliage on both top and back while center is nearest RHS 145 A on both surfaces. On older foliage the petiole the margin of both surfaces is RHS 143 A, and the center gradually lightens going toward middle to RHS 144A. The petiole is also heavily stippled with RHS 183 B on the inside and even numerous stipples of RHS 183 C on the back outside surface.

Flower description:

*Buds.*—One day prior to opening lighter than RHS N80 D; approximately 4.0 cm long, up to 1.0 cm wide, clavate with acute apex and longer thin base.

*Flowers.*—38 to 60 per scape; funnelform; 2.5 to 2.8 cm wide and 4.0 to 4.5 cm long, (distal flowers being smaller), persists for a normal period, usually one day on or cut from plant, and the scapes remain effective from early July into August. No detectable fragrance.

*Tepal.*—Two sets of three fused at the base; clavate with acute apex; entire; approximately 4 cm long and 1.0 cm wide, lighter than RHS N80 D on the outside of both sets with up to six slightly darker veins of about RHS N 80. Inside is slightly lighter than RHS N 78 D with up to six veins of RHS 78 D. Both sets of tepals have white margins at the basal one third on the inside.

*Gynoecium.*—Single; Style — 4.5 to 4.8 cm long, white, 1 mm diameter, curled at distal end; Stigma—1 mm to 2 mm in diameter, white.

*Androecium.*—Filaments — six, white, less than 1 mm in diameter and to 4.5 cm long; Anthers — 4 mm long, 1.0 mm wide, RHS 83 A.

*Pollen.*—Elliptical, less than 0.1 mm long, nearest RHS 15 A.

*Bracts.*—Lower bracts before flowers sessile with acute apex, protruding upward from scape at about 30 degree angle; normally up to 8 cm long and 3.0 cm wide, progressively smaller near first flowers on scape; outside surface center between RHS 143 A and RHS 143 B, with the outside surface margin RHS 137 B; inside surface center RHS N 144 A and the margin closest to RHS 137 A. Bracts subtending flowers protrude at about 70 degrees; initial bracts about 3.0 to 4.0 cm long and 1.8 cm wide; outside surface middle portion RHS 194 A with stippling of RHS 59 C, outside surface margin RHS 178 A. Inside surfaces identical in color to outside.

*Peduncle.*—One per mature division; erect 70 to 90 cm tall and to 8 mm in diameter, light green color RHS 145 B with reddish stippling and a light glaucous surface.

*Pedicel.*—Approximately 0.8 cm long, 2 mm wide, RHS 145 B with reddish stippling, curled downward.

*Fruit.*—A tri-valved capsule, approximately 2.5 cm long and 12 mm wide, RHS 183Bwith green undertones. More purple in higher light, and more green in lower light. Seeds are black, approximately 1 cm long and 2 mm wide.

Disease resistance: Resistance beyond that of other *hostas* has not been observed. The plant grows best with plenty of moisture and adequate drainage, but is able to tolerate some drought when mature. Hardiness at least from USDA zone 3 through 9, and other disease resistance is typical of that of other *hostas*.

I claim:

1. A new and distinct cultivar of ornamental *Hosta* plant named 'Eye Declare' as herein described and illustrated, with light yellowish leaf center, green margin with red stippling in the petiole and scape, suitable as a potted plant, for the garden, and for cut flower arrangements.

* * * * *

UNITED STATES PATENT AND TRADEMARK OFFICE

CERTIFICATE OF CORRECTION

PATENT NO. : PP 18,466 P2
APPLICATION NO. : 11/504333
DATED : January 29, 2008
INVENTOR(S) : Clarence Falstad It is certified that error appears in the above-identified patent and that said Letters Patent is hereby corrected as shown below:

Title Page item 57

In the abstract, the first sentence, "'Paradise Power'" should read --'Eye Declare'--

The final abstract should read as corrected:

--A new and distinct Hosta plant named 'Eye Declare' characterized by heart-shaped, large-sized, leaves with green margins, viridescent light yellowish leaf centers, vertical flower scapes well above foliage with numerous light lavender flowers, suitable for landscape, potted culture, or cut flower arrangements.--

Signed and Sealed this

Ninth Day of February, 2010

David J. Kappos

David J. Kappos
*Director of the United States Patent and Trademark Office*